United States Patent [19]

van der Stoel et al.

[11] Patent Number: 4,560,760
[45] Date of Patent: Dec. 24, 1985

[54] PROCESS FOR THE PREPARATION OF A LACTAM

[75] Inventors: Roland E. van der Stoel, Buchten; Marcel A. R. Bosma; Petrus H. J. Janssen, both of Geleen; Cornelis G. M. van de Moesdijk, Elsloo, all of Netherlands

[73] Assignee: Stamicarbon B.V., Geleen, Netherlands

[21] Appl. No.: 646,049

[22] Filed: Aug. 31, 1984

Related U.S. Application Data

[63] Continuation of Ser. No. 442,974, Nov. 19, 1982, abandoned.

[30] Foreign Application Priority Data

Nov. 21, 1981 [NL] Netherlands ............... 8105278

[51] Int. Cl.$^4$ .................................... C07D 201/08
[52] U.S. Cl. ............................... 546/243; 548/554
[58] Field of Search ....................... 546/243; 548/554

[56] References Cited

U.S. PATENT DOCUMENTS 3,235,562  2/1966  Shilling ............................ 546/243
4,162,267  7/1979  Fisher et al. ....................... 568/376
4,200,553  4/1980  Van Peppen et al. ............... 252/444

OTHER PUBLICATIONS

*Catalytic Hydrogenation Over Platinum Metals*, Paul N. Rylander, Academic Press, New York and London, 1967.
Chemical Abstracts, 90: 137194u (1979).
Chemical Abstracts, 93: 102064m (1980).

*Primary Examiner*—Norma S. Milestone
*Attorney, Agent, or Firm*—Cushman, Darby & Cushman

[57] ABSTRACT

Disclosed is a process for preparing a lactam which consists essentially in the reductive amination in the gas phase of an oxoalkane carboxylic acid having the formula

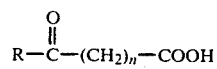

or an alkyl ester thereof, wherein R is an alkyl group having from 1 to 4 carbon atoms and n varies from 2 to 3, and wherein the reaction is carried out:
  A. in an atmosphere of hydrogen, and
  B. in the presence of a gas phase reactant selected from the group consisting of gaseous ammonia and a vaporized primary amine, and
  C. in the presence of a hydrogenation catalyst promoted with an alkali metal.

The alkali metal particularly preferred as a promoter is sodium.

7 Claims, No Drawings

PROCESS FOR THE PREPARATION OF A LACTAM

This is a continuation of application Ser. No. 442,974, filed Nov. 19, 1982, now abandoned.

This invention relates to a process for the preparation of a lactam by the reductive amination in the gas phase of a suitable oxoalkane carboxylic acid, or of an ester thereof, in the presence a promoted hydrogenation catalyst.

U.S. Pat. No. 3,235,562 discloses that a reductive amination can be implemented using hydrogenation catalysts suitable for gas phase reactions, such as nickel on a carrier such as kieselguhr, or copper chromite with barium as a promoter.

It has now been discovered that significantly higher yields of the desired product can be obtained if the hydrogenation catalyst is promoted with an alkali metal. Accordingly, this invention describes a process for preparing a 5- or 6-membered ring lactam which consists essentially in the reductive amination in the gas phase of an oxoalkane carboxylic acid, as starting material, having the formula

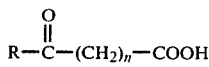

or an alkyl ester thereof, wherein R is an alkyl group having from 1 to 4 carbon atoms and n varies from 2 to 3, and wherein the reaction is carried out:

A. in an atmosphere of hydrogen, and
B. in the presence of a gas phase reactant selected from the group consisting of gaseous ammonia and a vaporized primary amine, and
C. in the presence of a hydrogenation catalyst promoted with an alkali metal.

The addition of an alkali metal to the hydrogenation catalyst as a promoter may itself be implemented by methodology known already in the art (see, for example, Preparation of Catalysts II, G. P. van den Berg en H. Th. Rijnten, Elsevier Amsterdam, 1979, page 265) by treating the catalyst with an alkali metal compound such as an alkali metal bicarbonate. The quantity of alkali metal in the catalyst can vary over a wide range, for example from about 0.01 to about 5 grams of the alkali metal per 100 g of the catalyst (including any carrier material). Advantageously, from about 0.1 to about 2 grams of the alkali metal is used per 100 grams of the catalyst. The alkali metal is preferably sodium.

Known hydrogenation catalyst metals such as metals from Groups IB and VIIIB of the periodic table, or compounds thereof, may be used. Catalyst compositions containing palladium, platinum or nickel are particularly suitable. If desired, the catalysts may be placed on a solid particulate carrier material. Suitable representative carriers are, for example, active carbon, graphite, silica, alumina, magnesia, and mixtures of these materials. When used with a carrier, the nobel catalyst metal should be present from 0.01 to 10 weight % of the total catalyst composition, advantageously from 0.1 to 5 weight percent and when use is made of nickel, the metal can be present from 5 to 80 weight % by preference 10 to 50 weight %.

The process of this invention may be carried out over a wide temperature range from about 50 to about 350° C. A range of from about 150° to about 250° C. is especially favorable.

In a manner similar to the known reductive amination previously mentioned, the reductive amination of this invention is performed using hydrogen together with ammonia or a primary amine having the formula

wherein R is an alkyl group having from 1 to 4 carbon atoms. The quantity of hydrogen used may vary between about 1 to about 25 moles of hydrogen per mole of the starting material. It is possible to use more than 25 moles of hydrogen per mole of the starting material, but no advantage results thereby. The quantity of the ammonia or primary amine may vary between about 1 and about 15 moles per mole of the starting material. It is also feasible to use more than 15 moles of ammonia or of primary amine per mole of the starting material, but, similarly, the result is not thereby improved. Preferred reactant quantity ranges, per mole of the starting material are about 1 to about 15 moles for hydrogen, and about 1 to about 5 moles for ammonia or for the primary amine.

If a primary amine is employed, the reaction product is an N-substituted lactam having a substituent corresponding to that on the primary amine. Any primary amine which will vaporize under the reaction conditions used may be employed. Moreover, a primary amine or ammonia per se need not be added, rather, it either may be formed in situ by the reduction of another compound, for example by reducing a nitro compound to the corresponding primary amine or by reducing hydrazine to ammonia.

The starting material may be selected from a variety of oxoalkane carboxylic acids or their esters. The process of this invention is particularly suitable for the reductive amination of gamma- or delta-oxoalkane carboxylic acids or their esters, such as 5-oxocaproic acid, 4-methyl-5-oxocaproic acid, levulinic acid, or the corresponding esters thereof.

The starting material is advantageously an ester of the desired acid, higher yields being obtained therewith than with the acid per se. The ester may be obtained as known in the art by esterifying the desired acid with an alcohol. When employing the ester, the corresponding alcohol of the ester group will be obtained as a by-product. Various ester groups may be used, such as lower alkyl having 1 to 3 carbon atoms, cycloalkyl such as cyclohexyl or cyclopentyl, or benzyl. It is preferred to use the lower alkyl esters made by esterifying the acid with methyl, ethyl, or isopropyl alcohol.

The reductive amination of this invention may be performed by using procedures known in the art for implementing gas phase reactions, such as passing the gaseous starting reaction mixture through a fixed or fluidized bed of the catalyst. The volumetric flow rate may be varied between about 0.001 and about 2 grams per hour of the starting material per milliliter of catalyst material (compacted volume).

By cooling the gaseous reaction mixture which results, a condensate is obtained, and the desired lactam can be separated therefrom by distillation or extraction. The lactams obtained are suitable in various applications such as the manufacture of plastics.

The invention will now be further explained by means of the following examples.

EXAMPLES I–V

A gaseous mixture of methyl 5-oxocaproate, hydrogen, and ammonia was passed for 165 hours through a vertical tubular reactor 25 mm in diameter and 400 mm in length containing a zone of 25 ml (compacted volume) of catalyst as described below and provided with a heating mantle. This gaseous mixture was obtained by evaporating liquid methyl 5-oxocaproate and mixing the vapor with hydrogen and gaseous ammonia. 6 moles of hydrogen and 3 moles of ammonia were used per mole of methyl 5-oxocaproate.

The catalyst was palladium on gamma-alumina promoted with sodium (Engelhard catalyst with 0.5 weight % of Pd and 0.4 weight % of Na, based on the weight of the Pd plus carrier). After operating times of 22, 91, 117, 142, and 164 hours, respectively, the conditions were held constant for a 1 hour period and the quality of methyl 5-oxocaproate that had entered the reactor and the quantity of the reaction product obtained (after condensation at 5° C.) were measured. The quantity of methyl 5-oxocaproate that had entered the reactor was determined by measuring the weight loss of the liquid methyl 5-oxocaproate. The composition of the reaction product was determined by gas chromatography. From this determination and by measuring the weight of the methyl 5-oxocaproate entering the reactor during the 1 hour period, the conversion of the oxo-ester and the yield of 6-methylpiperid-2-one was calculated.

The conversion is understood to mean the quantity of oxo-ester that is converted, that is, the quantity of oxo-ester that enters the reactor minus the quantity of oxo-ester in the condensed product, expressed as a percentage of the quantity of oxo-ester that enters the reactor. The yield of 6-methylpiperid-2-one is understood to mean the quantity of 6-methylpiperid-2-one in the condensed product expressed as a percentage of the quantity of 6-methylpiperid-2-one that theoretically can be formed from the converted quantity of oxo-ester.

The results and the reaction conditions are summarized in the table.

TABLE

| Example | I | II | III | IV | V |
|---|---|---|---|---|---|
| Operating time, in hours | 22 | 91 | 117 | 142 | 164 |
| Temperature, °C. | 200 | 200 | 240 | 240 | 240 |
| Space velocity in g oxo-ester per ml catalyst per hour | 0.16 | 0.16 | 0.13 | 0.13 | 0.13 |
| Conversion of oxo-ester in % | 98.2 | 68.5 | 92.3 | 85.6 | 79.3 |
| Yield of 6-methyl-piperid-2 one | 97.6 | 96.7 | 94.2 | 95.8 | 96.0 |

As this table shows, high conversions and consistently high yields were obtained with the inventive process.

COMPARATIVE EXAMPLE I

Example I was repeated without sodium in the catalyst. The yield was only 51%.

EXAMPLE VI

Using the same conditions described above in Example I, 6-methylpiperid-2-one was prepared from methyl 5-oxocaproate using, as catalyst, platinum on gamma-alumina promoted with sodium (Engelhard catalyst, 0.5 weight % Pt, 0.25 weight % Na, based on the weight of gamma alumina plus Pt). The conversion of oxo-ester was 97% and the yield of 6-methylpiperid-2-one was 90%.

What is claimed is:

1. A process for preparing a lactam which consists essentially in the reductive amination, in the gas phase, of an oxoalkane carboxylic acid ester having the formula

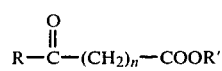

wherein R is an alkyl group having from 1 to 4 carbon atoms, R' is cycloalkyl, an alkyl group of from 1 to 3 carbon atoms or benzyl and n varies from 2 to 3, and wherein the reaction is carried out:
  A. in an atmosphere of hydrogen, and
  B. in the presence of a reactant, in the gas phase selected from the group consisting of gaseous ammonia and a vaporized primary amine, and
  C. in the presence of a hydrogenation catalyst metal selected from groups IB and VIIIB of the Periodic Table, or compounds thereof, promoted with sodium.

2. The process of claim 1, wherein about 0.1 to about 5 grams of sodium is used per 100 grams of the catalyst, based on the weight of the catalyst metal plus any carrier material.

3. The process of claim 2, wherein about 0.1 to about 2 grams of sodium is used per 100 grams of the catalyst, based on the weight of the catalyst metal plus any carrier material.

4. The process of claim 1, wherein said hydrogenation catalyst contains a metal selected from the group consisting of palladium, platinum, and nickel.

5. The process of claim 1, wherein said reductive amination is performed within a temperature range of about 150° to about 250° C.

6. The process of claim 1, wherein from about 1 to about 15 moles of ammonia or primary amine are employed per mole of said oxoalkane carboxylic acid ester.

7. The process of claim 1, wherein said ester is the methyl, ethyl, or isopropyl ester.